United States Patent
Kim

(10) Patent No.: US 11,007,932 B2
(45) Date of Patent: May 18, 2021

(54) DRIVER STATE WARNING APPARATUS, VEHICLE AND WARNING METHOD FOR DRIVER STATE

(71) Applicants: HYUNDAI MOTOR COMPANY, Seoul (KR); KIA MOTORS CORPORATION, Seoul (KR)

(72) Inventor: Juhyuk Kim, Suwon-si (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 0 days.

(21) Appl. No.: 16/788,654

(22) Filed: Feb. 12, 2020

(65) Prior Publication Data

US 2021/0031687 A1  Feb. 4, 2021

(30) Foreign Application Priority Data

Aug. 1, 2019 (KR) .......................... 10-2019-0094001

(51) Int. Cl.
| | |
|---|---|
| B60Q 9/00 | (2006.01) |
| B60R 11/04 | (2006.01) |
| G06K 9/00 | (2006.01) |
| A61M 21/00 | (2006.01) |
| A61N 7/00 | (2006.01) |
| A61B 5/00 | (2006.01) |
| A61B 5/18 | (2006.01) |

(52) U.S. Cl.
CPC .............. *B60Q 9/00* (2013.01); *A61B 5/0077* (2013.01); *A61B 5/18* (2013.01); *A61B 5/4836* (2013.01); *A61B 5/6893* (2013.01); *A61B 5/746* (2013.01); *A61M 21/00* (2013.01); *A61N 7/00* (2013.01); *B60R 11/04* (2013.01); *G06K 9/00845* (2013.01); *A61M 2021/0022* (2013.01); *A61M 2021/0083* (2013.01)

(58) Field of Classification Search
CPC ....... B60Q 9/00; A61B 5/0077; A61B 5/6893; A61B 5/4836; A61B 5/18; A61B 5/746; G06K 9/00845; B60R 11/04; A61N 7/00; A61M 21/00; A61M 2021/0022; A61M 2021/0083

See application file for complete search history.

(56) References Cited

U.S. PATENT DOCUMENTS

| | | | |
|---|---|---|---|
| 2016/0001781 A1* | 1/2016 | Fung ..................... | B60W 40/08 701/36 |
| 2017/0090475 A1* | 3/2017 | Choi ..................... | B60W 40/08 |
| 2017/0178304 A1* | 6/2017 | Matsuura ............. | H04N 5/2256 |

(Continued)

*Primary Examiner* — Ryan W Sherwin
(74) *Attorney, Agent, or Firm* — Brinks Gilson & Lione

(57) ABSTRACT

A driver state warning apparatus provides a safe and effective driving by non-contact haptic stimulus to a driver using an ultrasonic signal when the driver is in a drowsy or careless state. The driver state warning apparatus includes: a detector to obtain state information of a driver; a haptic stimulator to generate an ultrasonic beam and transmit the generated ultrasonic beam; and a controller to determine whether a state of the driver corresponds to a predetermined warning target state based on the obtained state information of the driver and provide a non-contact haptic stimulus by transmitting the ultrasonic beam toward the driver by controlling the haptic stimulator when the driver's state corresponds to the warning target state.

19 Claims, 17 Drawing Sheets

(56) References Cited

U.S. PATENT DOCUMENTS

2017/0332347 A1* 11/2017 Boss ................... H04W 24/08
2017/0365101 A1* 12/2017 Samec ................. G06T 19/006
2018/0005528 A1*  1/2018 Loeillet ................ G08G 1/165

* cited by examiner

PULSE SIGNAL APPLIED TO
TRANSDUCER ELEMENT(SHORT WAVE)

PULSE SIGNAL APPLIED TO
TRANSDUCER ELEMENT(LONG WAVE)

PULSE SIGNAL APPLIED TO
TRANSDUCER ELEMENT( INTENSITY: WEAK)

PULSE SIGNAL APPLIED TO
TRANSDUCER ELEMENT( INTENSITY:STRONG)

DRIVER STATE WARNING APPARATUS, VEHICLE AND WARNING METHOD FOR DRIVER STATE

CROSS-REFERENCE TO RELATED APPLICATION

This application claims priority to and the benefit of Korean Patent Application No. 10-2019-0094001, filed on Aug. 1, 2019, the entire contents of which are incorporated herein by reference.

FIELD

The present disclosure relate to a driver state warning apparatus, vehicle and warning method for driver state.

BACKGROUND

The statements in this section merely provide background information related to the present disclosure and may not constitute prior art.

Drivers' drowsiness, neglect of forward attention, and cell phone operation while driving are one of the main causes of traffic accidents. Therefore, recently, a technology for a driver state warning that detects a driver's state and outputs a warning when the driver is not focused on driving to induce safe driving is being developed.

However, we have discovered that the existing driver status warning technology has a limitation in the manner of outputting a warning, and a driver who is familiar with the existing warning output method often ignores the warning even if the warning is output.

Therefore, it is difficult to effectively induce the driver's safe driving with this limited warning output.

SUMMARY

The present disclosure provides a driver state warning apparatus, vehicle and warning method for driving state capable of inducing an effective and direct safe driving by providing a haptic stimulus to the driver in a non-contact manner by using ultrasonic signals when the driver is in a drowsy or inattentive state.

In accordance with an aspect of the present disclosure, a driver state warning apparatus includes: a detector configured to obtain state information of a driver; a haptic stimulator configured to generate an ultrasonic beam and transmit the generated ultrasonic beam; and a controller configured to determine whether a state of the driver corresponds to a predetermined warning target state based on the obtained state information of the driver. In particular, the controller is configured to provide a non-contact haptic stimulus by transmitting the ultrasonic beam toward the driver by controlling the haptic stimulator when the state of the driver corresponds to the warning target state.

The haptic stimulator may include a transducer array converting an electrical signal into an ultrasonic signal.

The detector may include a camera configured to capture the driver's image.

The controller may determine a target position to transmit the ultrasonic beam from the image of the driver, and controls the transducer array to transmit the ultrasonic beam to the target position.

In one form, the transducer array may include a plurality of transducer elements which are divided into a plurality of groups based on body parts of the driver, and the controller may transmit a control signal to transducer elements of a group corresponding to a body part of the driver included in the target position.

In another form, the controller may match and store the location information of the driver's image and the location information of the transducer array, and transmit a control signal to the transducer array matched to the target position.

The controller may control the transducer array to generate a directional ultrasonic beam directed towards the target position.

In other form, the controller may determine whether the driver's state corresponds to at least one of a drowsy state or a careless state based on the driver's image and transmit the ultrasonic beam towards at least one body part of the driver by controlling the haptic stimulator when the driver's state corresponds to at least one of the drowsy state or the careless state.

The controller may transmit the ultrasonic beam towards an eye of the driver by controlling the haptic stimulator when the driver's state corresponds to the drowsy state.

The controller may transmit a short wave ultrasonic beam by controlling the haptic stimulator to provide a vibration stimulus to the driver's eyes.

The controller may determine whether the driver's state corresponds to the careless state based on the driver's image.

The controller may transmit the ultrasonic beam from a direction of the driver's face by controlling the haptic stimulator when the state of the driver corresponds to the careless state.

The controller may transmit a long wave ultrasonic beam by controlling the haptic stimulator to provide a resistive stimulus in a direction opposite to the direction currently facing the driver's face.

The controller may transmit the ultrasonic beam toward the driver's eyes by controlling the haptic stimulator when the state of the driver corresponds to the careless state.

The controller may stop transmitting the ultrasonic beam after start of transmitting the ultrasonic beam when the driver's state does not correspond to at least one of the drowsy state or the careless state.

In accordance with another aspect of the present disclosure, a vehicle includes: a detector configured to obtain information related to a driver state; a haptic stimulator configured to generate an ultrasonic beam and transmit the generated ultrasonic beam; and a controller configured to determine whether the driver state corresponds to a predetermined warning target state based on the obtained information related to the driver state, and provide a non-contact haptic stimulus by transmitting the ultrasonic beam toward the driver by controlling the haptic stimulator when the driver state corresponds to the warning target state.

The haptic stimulator may include a transducer array converting an electrical signal into an ultrasonic signal.

In accordance with an aspect of the present disclosure, a driver state warning method includes: obtaining, by a detector, information regarding a driver state; determining, by a controller, whether the driver state corresponds to a predetermined warning target state; and providing, by the controller, a non-contact haptic stimulus by transmitting the ultrasonic beam toward the driver by controlling a haptic stimulator including a plurality of transducer arrays when the driver state corresponds to the warning target state.

Obtaining information related to a driver state may include capturing the driver's image by using a camera.

Transmitting the ultrasonic beam toward the driver may include determining a target position to transmit the ultrasonic beam from the driver's image, and controlling the plurality of the transducer arrays to transmit the ultrasonic beam to the target position.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
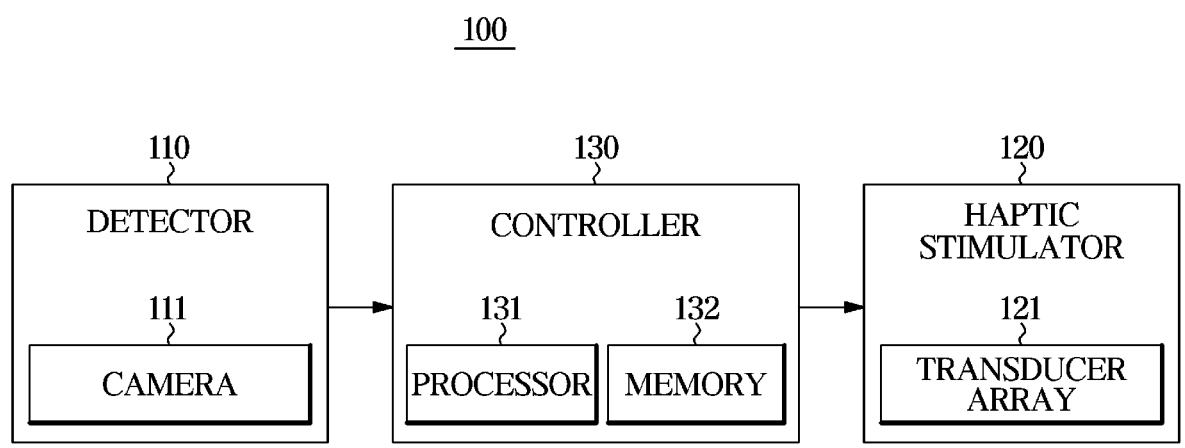
FIG. 1 is a control diagram illustrating a driver state warning apparatus.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Configurations and drawings described herein are examples of the disclosure, and there may be various modifications that can replace the exemplary forms and drawings of the present disclosure at the time of filing of the present application.

Also, the terminology used herein is for the purpose of describing particular forms only and is not intended to be limiting of the disclosure. Singular expressions include plural expressions unless the context clearly indicates otherwise. As used herein, the terms "comprise", "comprise" or "have" are intended to designate that the features, numbers, steps, actions, components, parts, or combinations thereof described in the specification are present, and it does not preclude the existence or addition of one or more other features or numbers, steps, operations, components, parts or combinations thereof in advance.

In addition, terms such as "~part", "~group", "~block", "~member", "~module" may refer to a unit for processing at least one function or operation. For example, the terms may refer to at least one hardware processed by at least one piece of hardware such as a field-programmable gate array (FPGA)/application specific integrated circuit (ASIC), at least one software stored in a memory, or a processor.

The references attached to the steps are used to identify the steps. These references do not indicate the order between the steps. Each step is performed in a different order than the stated order unless the context clearly indicates a specific order.

On the other hand, the disclosed forms may be implemented in the form of a recording medium for storing instructions executable by a computer. Instructions may be stored in the form of program code and, when executed by a processor, may generate a program module to perform the operations of the disclosed forms. The recording medium may be implemented as a computer-readable recording medium.

Computer-readable recording media include all kinds of recording media having stored thereon instructions which can be read by a computer. For example, there may be a read only memory (ROM), a random access memory (RAM), a magnetic tape, a magnetic disk, a flash memory, an optical data storage device, and the like.

Hereinafter, a driver state warning apparatus, a vehicle, and a driver state warning method according to an aspect will be described in detail with reference to the accompanying drawings.

Figure 2:
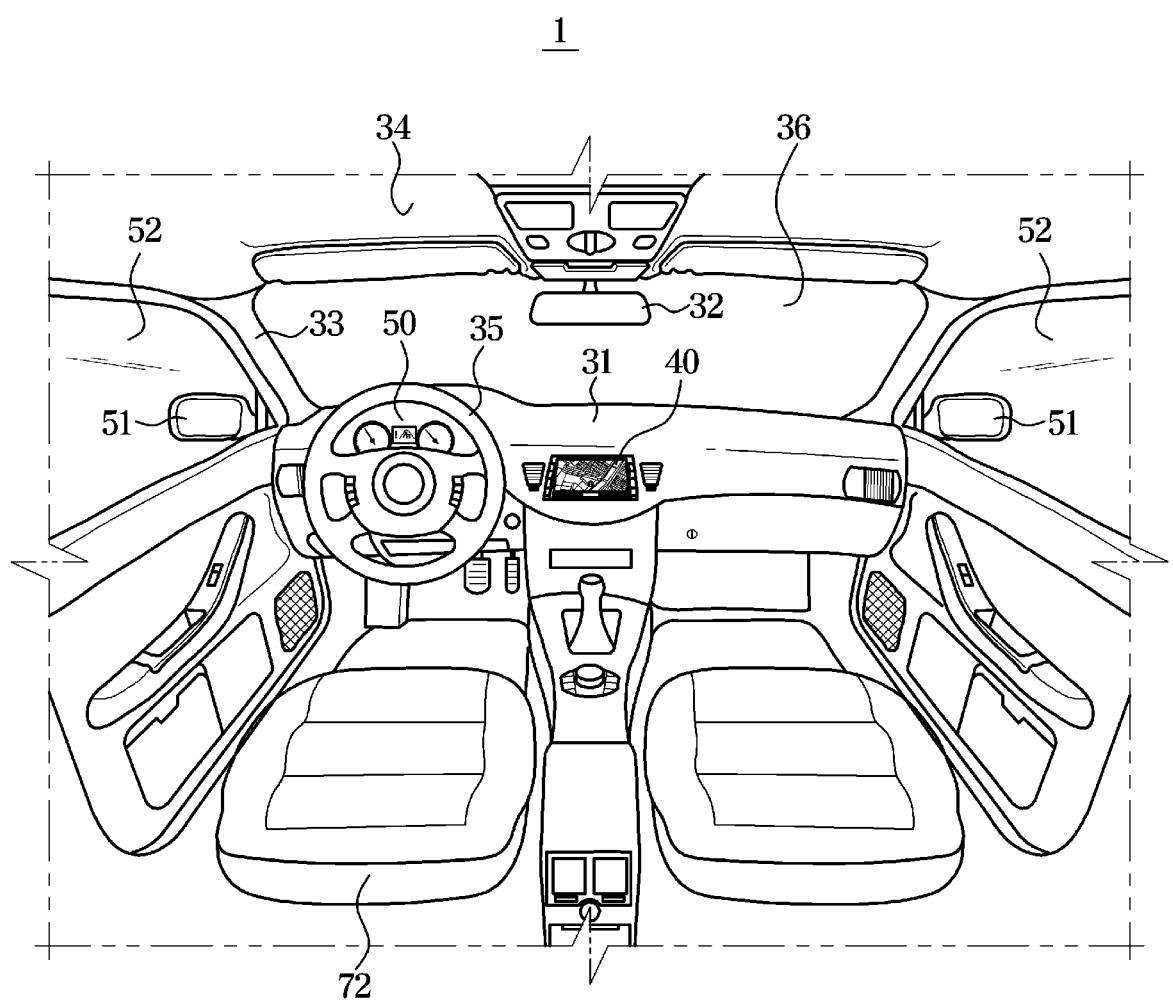
FIG. 2 is a diagram illustrating an internal configuration of a vehicle.
Figure 3:
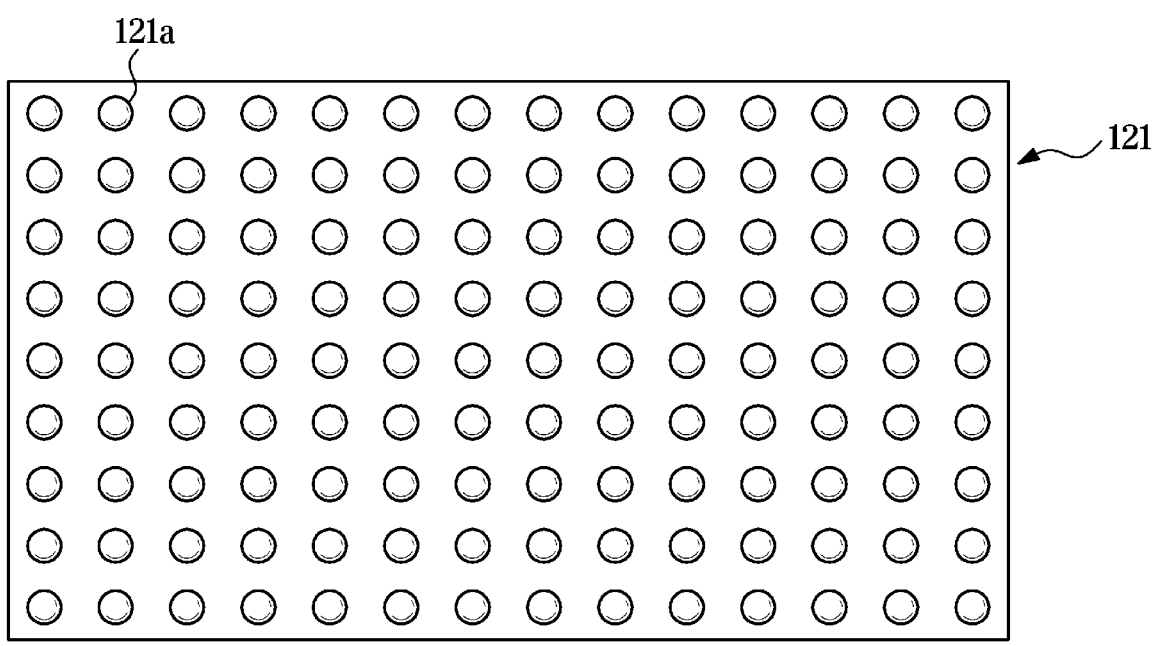
FIGS. 3 and 4 are views illustrating examples of a haptic stimulator applied to a driver state warning apparatus.
Figure 4:
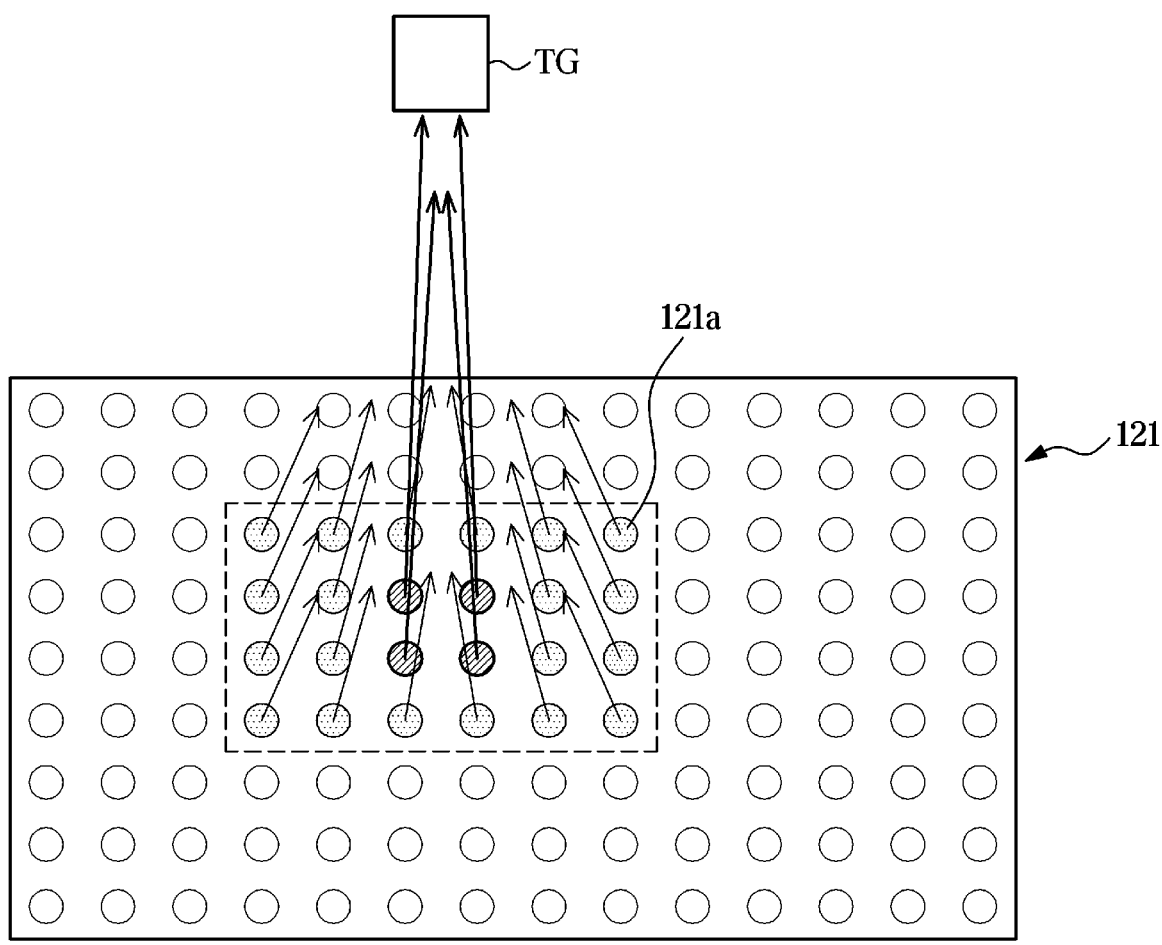

FIG. 1 is a control diagram illustrating a driver state warning apparatus according to one form of the present disclosure, FIG. 2 is a diagram illustrating an internal configuration of a vehicle according to another form, and FIGS. 3 and 4 are views illustrating examples of a haptic stimulator applied to a driver state warning apparatus according to other form of the present disclosure.

Referring to FIG. 1, in an aspect of the present disclosure, a driver state warning apparatus includes: a detector configured to obtain information related to a driver state; a haptic stimulator configured to generate an ultrasonic beam and transmit the generated ultrasonic beam; and a controller configured to determine whether the driver state corresponds to a predetermined warning target state based on the obtained information related to the driver state, and provide a non-contact haptic stimulus by transmitting the ultrasonic beam toward the driver by controlling the haptic stimulator when the driver state corresponds to the warning target state.

The detector 110 may include at least one of various sensors capable of acquiring information related to a driver's state. For example, the detector 110 may include an image sensor that captures an driver's image, that is, a camera 111. The camera may be an infrared camera or a general visible light camera. In addition, the camera 111 may capture a moving image, or may capture a still image according to a predetermined period.

In addition, the camera 111 may be a stereo camera capable of acquiring depth information.

The vehicle 1 includes the driver status warning apparatus 100 described above. Hereinafter, examples of positions where the configurations of the driver state warning apparatus 100 are provided in the vehicle 1 will be described together.

The camera 111 may be provided at a position capable of capturing an image of the driver. Referring to FIG. 2, the camera 111 may be provided in the cluster area 50 facing the driver, or may be provided in the room mirror 32. It may be provided on the windshield 36, the headlining 34 or the center fascia 31. The driver's face or the position where the image including the driver's face and hand may be captured may be used, and no other limitation is provided.

In addition, the detector 110 may include a biosignal sensor that detects a biosignal of a driver. As the biological signal sensor, a sensor for measuring signals such as electroencephalogram (EEG), electromyogram (EMG), electrocardiogram (ECG), and electrocardiogram (EOG) may be employed.

The biosignal sensor may be provided in the steering wheel 35 according to the measurement item, or may be provided in a separate wearable device.

The detector 110 is not limited to the above-described example, it is only desired to obtain information on the driver's state, and there are no other limitations on the types of the detector 110.

The haptic stimulator 120 may provide a haptic stimulus to the driver without a direct body contact by using an ultrasonic signal. Ultrasonic signals refer to signals that are not audible to humans with frequencies that are beyond the audible range of humans. In general, a signal with a frequency over 20 kHz is called an ultrasonic signal.

The frequency of the ultrasonic signal generated by the haptic stimulator 120 may be determined in consideration of the range in which the sensory receptors of human skin can sense. For example, the haptic stimulator 120 may transmit an ultrasonic signal of 40 kHz or more in the air, and the vibration by the ultrasonic signal is transmitted through the air as a medium.

Referring to the example of FIG. 3, the haptic stimulator 120 may include a transducer array 121 that converts an electrical signal into an ultrasonic signal. The plurality of transducer elements 121a constitutes the two-dimensional transducer array 121.

The plurality of transducer elements 121a may employ at least one of various methods of generating an ultrasonic signal. For example, the transducer element 121a may be a magnetostrictive ultrasonic transducer (MUT) using a magnetostrictive effect of a magnetic material, a piezoelectric ultrasonic transducer (PUT) or a piezoelectric type using a piezoelectric effect of a piezoelectric material. It may be implemented as a micromachined ultrasonic transducer (pMUT). It can also be implemented as a Capacitive Micromachined Ultrasonic Transducer (cMUT), which generates ultrasonic waves using vibrations of hundreds or thousands of microfabricated thin films. There is no other limitation on the ultrasonic generation method of the transducer element 121a.

As shown in FIG. 4, the controller 130 may form an ultrasonic beam by adjusting a phase and an amplitude such that ultrasonic signals transmitted from the plurality of transducer elements 121a are simultaneously focused and reach the target position TG.

When the ultrasonic beam reaches the target position TG, the body part of the driver at the target position TG may feel the haptic stimulus. That is, the driver can feel the vibration transmitted through the air as a medium without directly contacting the transducer element 121a.

A more specific manner in which the haptic stimulator 120 provides haptic stimulation to the driver will be described later.

The controller 130 includes at least one memory 131 for storing a program for performing the above-described operations and the operations described below, and various data for executing the program, and at least one processor 132 for executing the stored program. The memory 131 and the processor 132 may be integrated on one chip or may be physically separated.

In addition, when a plurality of the memory 131 and the processor 132 is provided, the plurality of memory 131 and the plurality of processors 132 may be integrated on one chip or included in one module. It may be physically separated, such as integrated on another chip or included in another module.

The controller 130 may determine whether the driver's state corresponds to a predetermined warning target state based on the information related to the driver's state acquired by the detector 110. The predetermined warning state may include a drowsiness state and a careless state, and a careless state includes at least one of the driver's head does not face forward for a fixed time, the driver's pupils do not look forward, such as a state in which the driver's pupils do not look forward (forward), and the driver is looking forward, but the driver's hands or one hand is more than a predetermined time on the steering wheel (35) apart.

For example, when the detector 110 includes the camera 111, it is determined whether the driver's state corresponds to a drowsy state or whether the driver's state corresponds to a careless state based on the image of the driver captured by the camera.

The controller 130 may analyze the image of the driver to determine whether the driver's pupil is not visible for a predetermined time or more. To this end, the controller 130 detects a pupil by applying an object recognition algorithm to the driver's image, and if the detected pupil is not seen for a predetermined time or more, the controller 130 may determine that the driver's state is drowsy. Alternatively, when the pupil is not detected for a predetermined time or more, it may be determined that the driver's state is drowsy.

Alternatively, the controller 130 may analyze the driver's image and determine whether the driver's head moves according to a predetermined pattern.

The dozing person's head can move according to certain patterns. Accordingly, the controller 130 may store the specific pattern and determine that the driver's state is a drowsy state when the driver's head movement pattern shown in the image of the driver corresponds to the stored specific pattern.

As another example, when the detector 110 includes a biosignal sensor, it may be determined that the driver's state corresponds to a drowsiness state when the biosignal value output by the biosignal sensor corresponds to a biosignal value that appears when a person is in drowsy state.

In addition, the controller 130 may analyze the image of the driver to determine whether the driver's state corresponds to the careless state. For example, the driver's pupil may be detected from the driver's image, and the driver's gaze may be determined based on the detected position of the pupil. If it is determined that the driver's gaze does not face forward, it may be determined that the driver's state corresponds to the careless state. Alternatively, it is possible to determine that the driver's state corresponds to a careless state when the state in which the driver's gaze does not face forward continues for a predetermined time or more.

As another example, the controller 130 detects the driver's face from the driver's image and determines whether the driver's head is facing forward based on the detected contour of the face or the position of the eyes, nose, mouth within the face, or face movement. If it is determined that the driver's head does not face forward, it may be determined that the driver's state corresponds to the careless state. Alternatively, it is possible to determine that the driver's state corresponds to a careless state when the state in which the driver's head does not face forward continues for a predetermined time or more.

As another example, the controller 130 may detect the driver's hand in the driver's image and determine that the driver's state corresponds to the careless state when the detected driver's hand is separated from the steering wheel 35 for more than a predetermined time.

On the other hand, when it is determined that the driver's state corresponds to the careless state, when the surrounding situation is checked through the room mirror 32, the side mirror 51, or the window 52 of the vehicle 1 for a predetermined time of grace, it may be excluded from careless state.

If it is determined that the driver's state corresponds to a drowsy state or an careless state, the controller 130 may output a warning by controlling the haptic stimulator 120 to provide a haptic stimulus to the driver.

As described above, the haptic stimulator 120 may transmit the focused ultrasonic beam to the target location, and the vibration by the transmitted ultrasonic beam may reach the target location using air as a medium. Thus, the driver at the target position can feel the haptic stimulus in a non-contact manner without contacting the haptic stimulator 120.

Existing methods of alerting the driver by hearing or vision have made it difficult to effectively drive safety due to the driver not paying attention to the warning itself or becoming familiar with the warning. In addition, since the general haptic stimulus is transmitted in a contact manner, it is difficult to apply it in a driving environment because it is inconvenient to wear specific equipment to give the haptic stimulus to the driver.

Existing methods of alerting the driver by hearing or vision have made it difficult to effectively drive safety due to the driver not paying attention to the warning itself or becoming familiar with the warning. In addition, since the general haptic stimulus is transmitted in a contact manner, it is difficult to apply it in a driving environment because it is inconvenient to wear specific equipment to give the haptic stimulus to the driver.

However, according to the driver state warning apparatus 100 according to one form, it is possible to effectively remind the driver's attention by providing the driver with a haptic stimulus in a non-contact manner, and effectively direct safe driving by adjusting the direction of the haptic stimulus as described below. Detailed haptic stimulus providing method will be described later.

Figure 5:
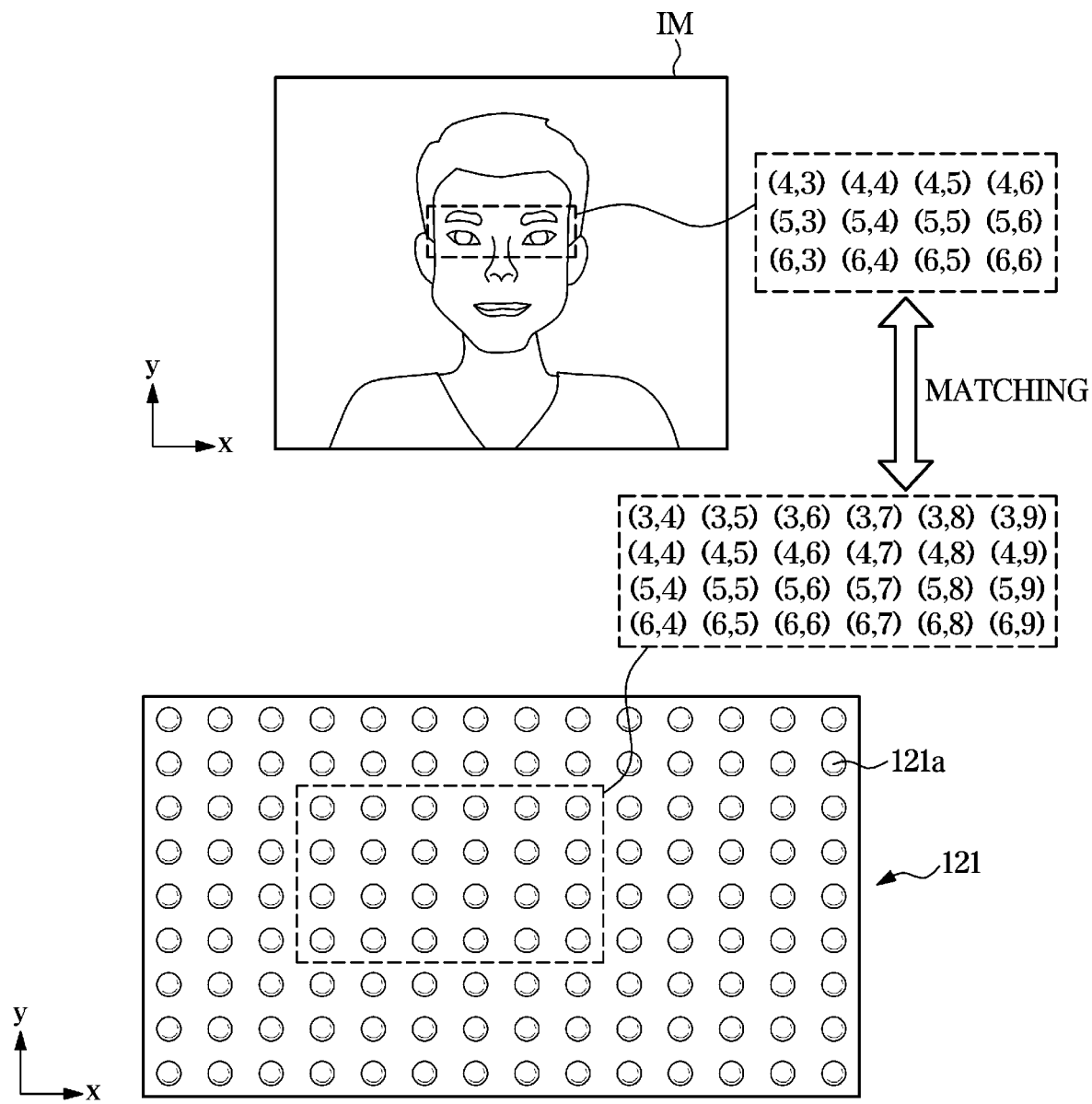
FIG. 5 is a diagram illustrating a positional correspondence relationship between a transducer array and a driver image included in a driver state warning apparatus.

FIG. 5 is a diagram illustrating a positional correspondence relationship between a transducer array and a driver image included in a driver state warning apparatus, according to one form.

As referring to FIG. 5, the haptic stimulator 120 may include a plurality of transducer elements 121*a* in which m×n (m, n is an integer of 2 or more) constitutes a two-dimensional array.

The controller 130 may perform calibration to match the position information of the individual transducer element 121*a* with the position information of the driver's image IM. Specifically, both the position of the driver's image IM and the position of the individual transducer element 121*a* may be represented by two-dimensional coordinates, and for each position of the driver's image IM, the transducer element corresponding to the position (121*a*) can be matched. Here, the position of the transducer element 121*a* corresponding to the position of the driver's image IM may mean the position of the transducer element 121*a* used to transmit the ultrasonic beam to the actual space corresponding to the position.

Alternatively, such position correspondence may be stored in advance in the memory 131.

There may be a plurality of transducer elements 121*a* corresponding to one position in the driver's image IM, and one transducer element 121*a* may correspond to several positions in the driver's image IM.

As illustrated in FIG. 5, the controller 130 may detect a region corresponding to the driver's eye in the driver's image IM, and the position of the detected region may be expressed by two-dimensional coordinates. The controller 130 may obtain the position of the transducer element 121*a* matched to the corresponding position based on the calibration result.

When the controller 130 determines that the driver's state corresponds to the drowsiness state based on the driver's image IM, a control signal may be transmitted to the haptic stimulator 120 so that the transducer element 121*a* at the position matched with the eye position in the driver's image IM transmits an ultrasonic signal.

Such calibration is performed in the manufacturing stage of the driver state warning apparatus 100, and the position correspondence relationship may be stored in the memory 131, or may be made by the controller 130 at the first installation or the first use, and may be redone if relative position between the camera 111 and the haptic stimulator 120 changes.

Alternatively, the plurality of transducer elements 121*a* constituting the transducer array 121 may be divided into a plurality of groups according to body parts of the driver.

Figure 6:
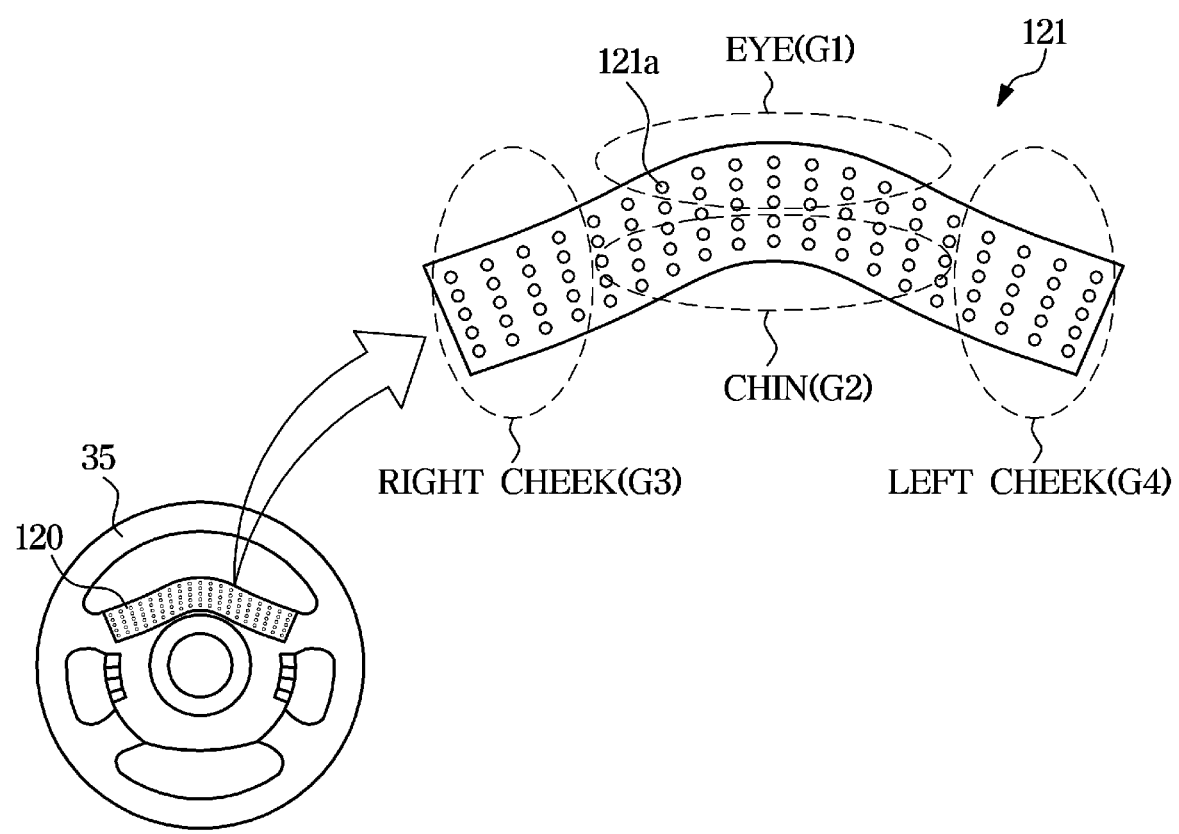
FIGS. 6 and 7 are views illustrating an example in which a plurality of transducer elements are divided into a plurality of groups according to body parts of a driver in the driver state warning apparatus.
Figure 7:
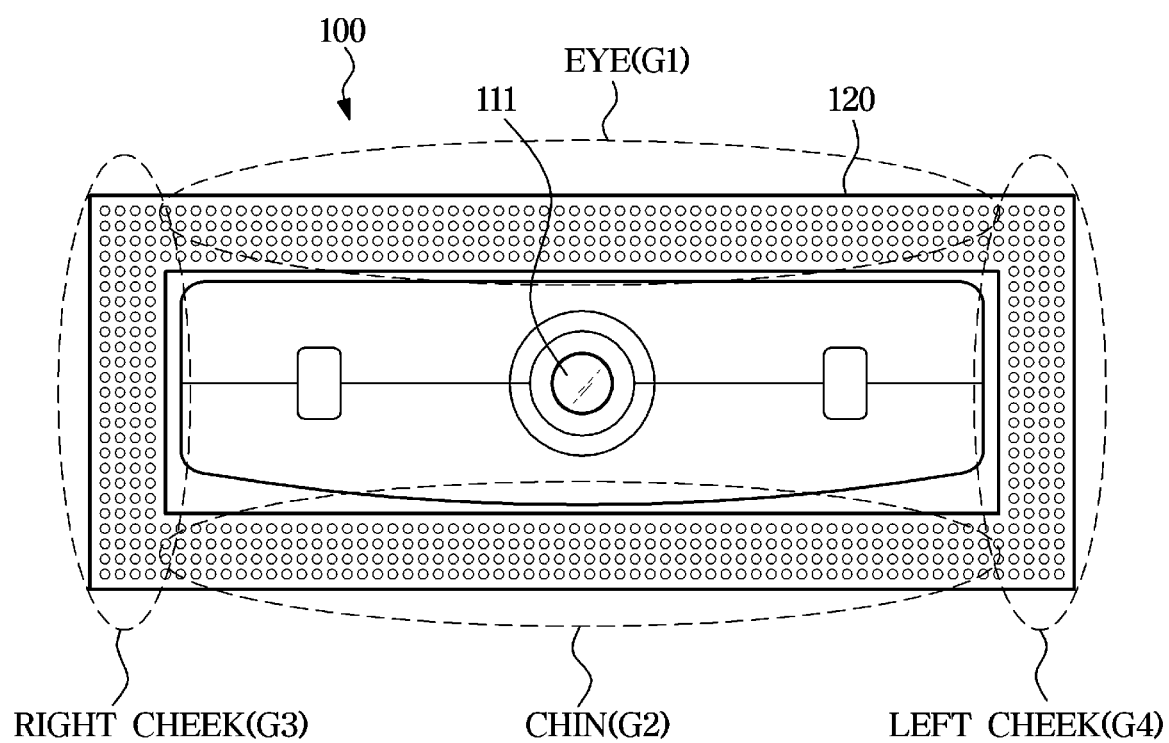

FIGS. 6 and 7 are views illustrating an example in which a plurality of transducer elements are divided into a plurality of groups according to body parts of a driver in the driver state warning apparatus according to one form.

Since the driver is driving in a sitting position, the driver's position does not change significantly while driving. Thus, as illustrated in FIGS. 6 and 7, the plurality of transducer elements 121*a* are divided into a plurality of groups G1, G2, G3, and G4 according to the driver's body part, and a haptic stimulus is provided at a certain part. When it is determined to which region the haptic stimulus is to be provided, the transducer elements 121*a* of the group corresponding to the region may be controlled to transmit an ultrasonic signal.

For example, when the body parts to which the ultrasonic signal is to be transmitted are eyes, chin, right cheeks, and left cheeks according to the driver's state, the plurality of transducer elements 121*a* correspond to the first group G1 corresponding to the eyes. It may be divided into a second group G2 corresponding to the chin, a third group G3 corresponding to the right cheek, and a fourth group G4 corresponding to the left cheek.

The plurality of transducer elements 121*a* included in the first group G1 are used to transmit ultrasonic signals to the driver's eyes. The plurality of transducer elements 121*a* included in the second group G2 are used to transmit ultrasonic signals to the chin of the driver. The plurality of transducer elements 121*a* included in the third group G3 are used to transmit ultrasonic signals to the right cheek of the driver. The plurality of transducer elements 121*a* included in the fourth group G4 are used to transmit ultrasonic signals to the left cheek of the driver. At this time, it is also possible for each group to share a common transducer element 121a.

If desired, it is possible to add more groups corresponding to other body parts such as the driver's arm or hand.

Meanwhile, the haptic stimulator 121 may be physically separated from the remaining components of the driver state warning apparatus 100 and provided at a suitable position for transmitting an ultrasonic signal to a specific body part of the driver. For example, as illustrated in FIG. 6, the haptic stimulator 121 may be provided at the steering wheel 35 facing the driver. The haptic stimulator 121 may be provided at the A-pillar 33 and may be provided at any position where the ultrasonic beam may be sent toward the driver, such as the cluster region 50, the windshield 36, or the center fascia 31.

Alternatively, the haptic stimulator 121 and the remaining components may constitute one physical module. In this case, as illustrated in FIG. 7, the plurality of transducer elements 121a constituting the transducer array 121 may be disposed in a form surrounding the physical module constituting the driver state warning apparatus 100. In this case, the plurality of transducer elements 121a may be divided into a first group G1, a second group G2, a third group G3, and a fourth group G4.

FIGS. 8 to 13 are views illustrating examples of signals input to individual transducer elements.

The plurality of transducer elements 121a constituting the transducer array 121 can be individually controlled. Accordingly, phase, intensity (amplitude), etc. may be adjusted differently for each frequency of the ultrasonic signal generated from the individual transducer element 121a.

Figure 8:
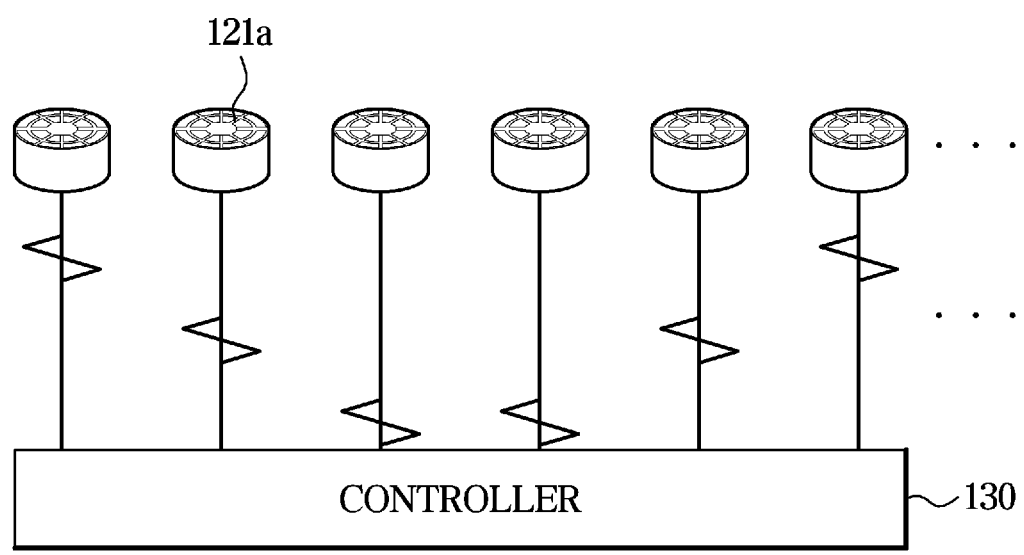
FIGS. 8 and 9 are views illustrating examples of signals input to individual transducer elements.

As shown in FIG. 8, an ultrasonic beam in which a signal is focused to the center may be generated by controlling the phase differently by giving a time delay to the ultrasonic transmission from the center to the periphery.

Figure 9:
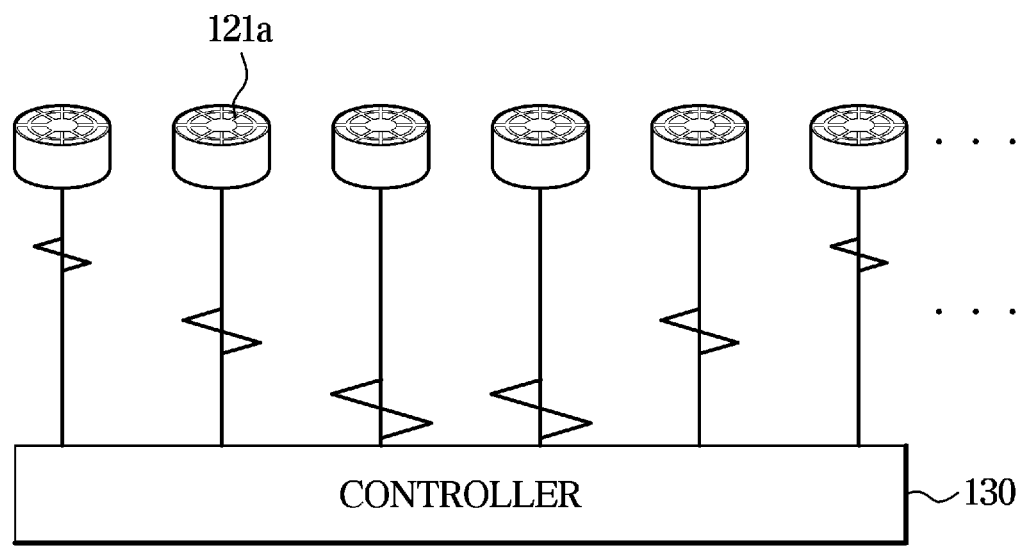

In addition, as shown in FIG. 9, the intensity of the ultrasonic signal may be adjusted differently for each individual transducer element 121a. The strength of the signal in the center may be the strongest and the strength of the signal may be weakened toward the periphery.

In the above-described example, an example in which an ultrasonic signal is transmitted to a desired body part by using the transducer element 121a allocated to each body part is illustrated, however it is also possible to control to generate a directional ultrasonic beam directed to a desired body part by controlling the ultrasonic phase by adjusting the timing of transmitting the ultrasonic signal from each transducer element 121a.

Figure 10:
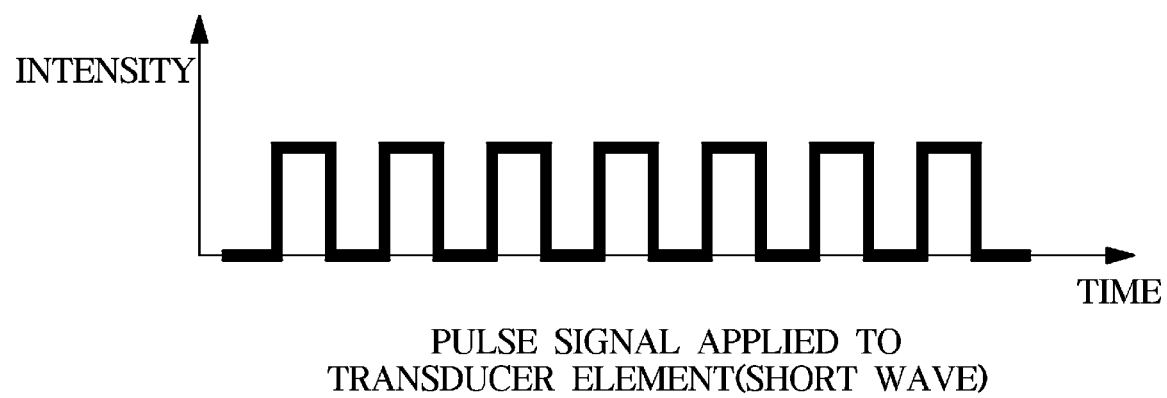
FIG. 10 is a view illustrating a short wave signal applied to transducer elements.

On the other hand, when generating the ultrasonic signal by the pulse control, as shown in FIG. 10, a short wave may be applied to the transducer element 121a to provide a vibrating stimulation of a feeling such as tapping.

Figure 11:
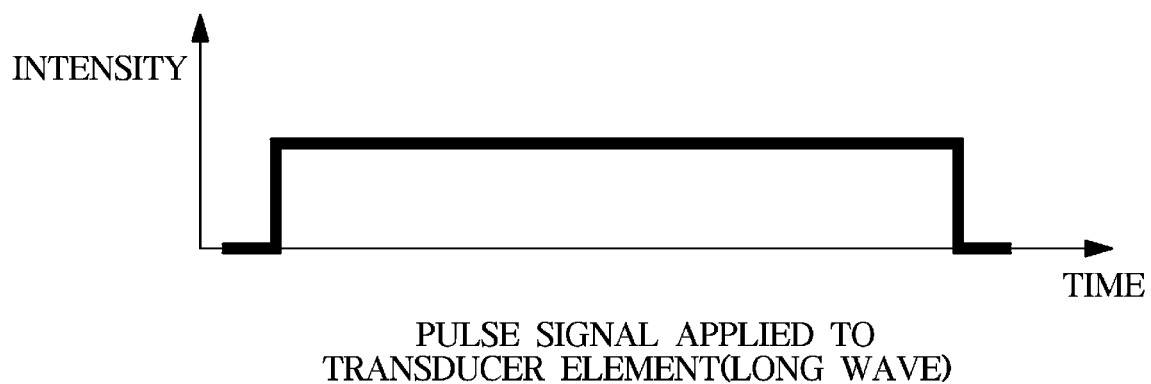
FIG. 11 is a view illustrating a long wave signal applied to transducer elements.

Alternatively, as illustrated in FIG. 11, a resistance stimulus having a feeling such as pushing the long wave to the transducer element 121a may be provided.

Figure 12:
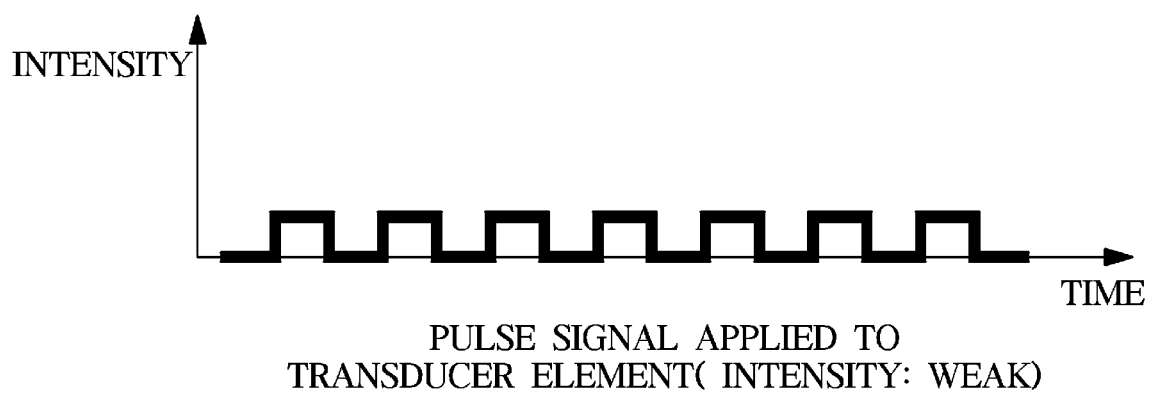
FIG. 12 is a view illustrating a pulse signal having weak intensity as applied to transducer elements.
Figure 13:
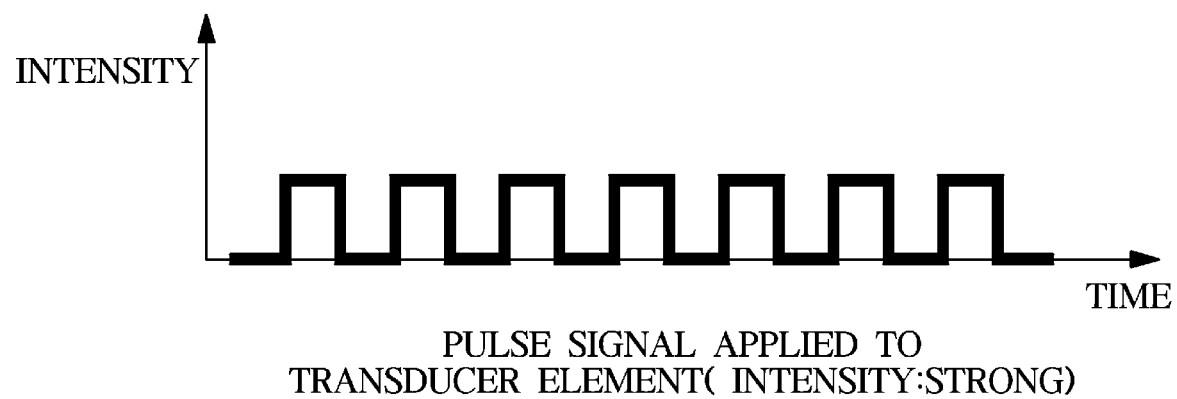
FIG. 13 is a view illustrating a pulse signal having strong intensity as applied to transducer elements.

Alternatively, as illustrated in FIGS. 12 and 13, the intensity of the ultrasonic signal may be controlled by weakly or strongly adjusting the intensity of the pulse applied to the individual transducer element 121a.

That is, the controller 130 may generate the appropriate haptic stimulus suitable for the driver's state by individually controlling the phase, intensity, speed, etc. of the ultrasonic signal with respect to the plurality of transducer elements 121a.

Figure 14:
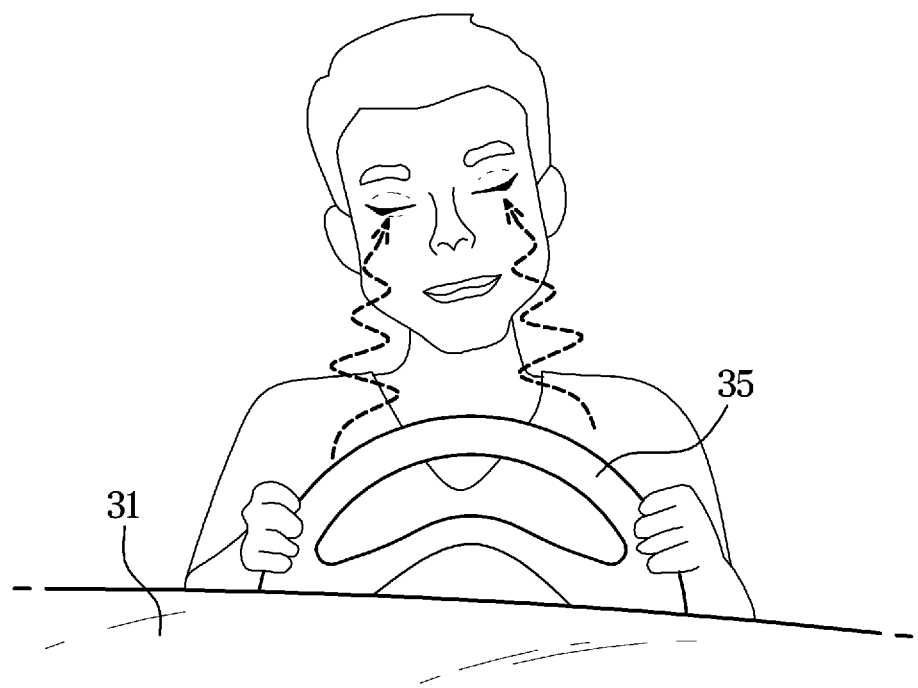
FIGS. 14 and 15 are views illustrating examples of a method in which a driver state warning apparatus provides a haptic stimulus to a driver.
Figure 15:
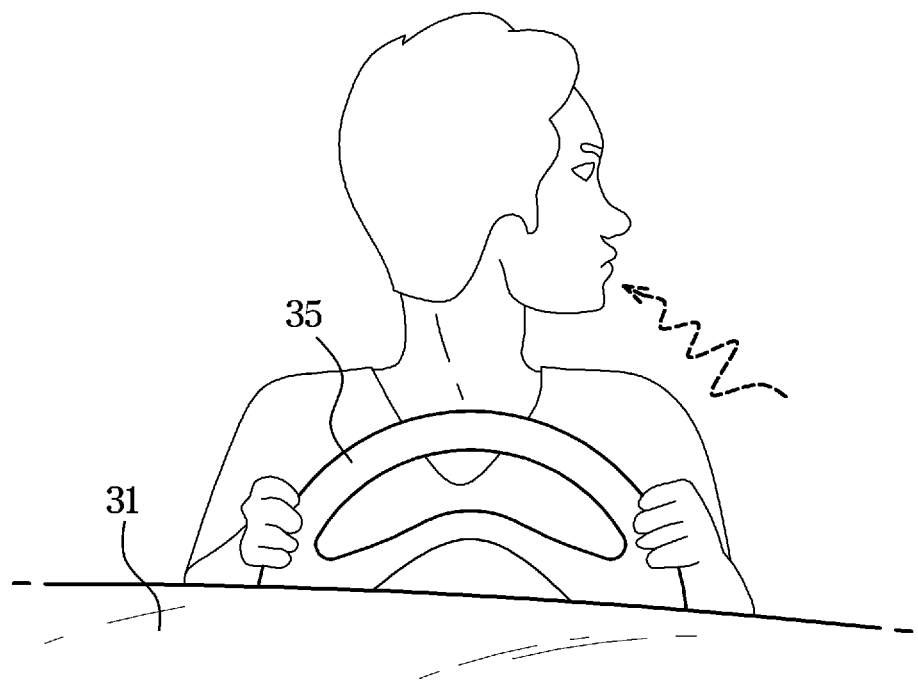

FIGS. 14 and 15 are views illustrating examples of a method in which a driver state warning apparatus provides a haptic stimulus to a driver, according to one form. In this example, the case where the haptic stimulator 120 is mounted on the steering wheel 35 is taken as an example.

When the controller 130 determines that the driver's state corresponds to the drowsy state by analyzing the driver's image IM, the controller 130 controls the haptic stimulator 120 to transmit an ultrasonic beam toward the driver's eyes. As described above, the eye region may be detected from the driver's image IM, and a control signal may be applied to the transducer element 121a at a position corresponding to the detected eye region to transmit the ultrasonic beam. At this time, the driver's eyes can feel the vibration stimulus by transmitting the short-wave ultrasonic beam.

In addition, as shown in FIG. 6, when the haptic stimulator 120 is divided into a plurality of groups G1, G2, G3, and G4 according to the driver's body part, the controller 130 corresponds to a first eye corresponding to the driver's eyes. The control signal may be applied to the transducer elements 121a of the group G1.

In addition, as shown in FIG. 6, when the haptic stimulator 120 is divided into a plurality of groups G1, G2, G3, and G4 according to the driver's body part, the controller 130 corresponds to a first eye corresponding to the driver's eyes. The control signal may be applied to the transducer elements 121a of the group G1.

In addition, when the controller 130 analyzes the driver's image IM and determines that the driver's state is inadvertent and that the driver's head is not facing forward but toward the left side (driver's standard), as shown in FIG. 15, the haptic stimulator 120 is controlled to transmit an ultrasonic beam to the left cheek of the driver. That is, the ultrasonic beam can be transmitted from the direction that the driver's face faces.

To this end, the left cheek area may be detected from the driver's image IM, and a control signal may be applied to the transducer element 121a at a position corresponding to the detected left cheek area to transmit the ultrasonic beam. At this time, the ultrasonic beam is incident on the left cheek of the driver, but the direction thereof may be controlled to face the right side of the driver. In addition, by transmitting a long wave ultrasonic beam, the driver can feel the resistance in the right direction. That is, the driver's face can feel the resistance in the opposite direction from the current direction.

In addition, as shown in FIG. 6, when the haptic stimulator 120 is divided into a plurality of groups G1, G2, G3, and G4 according to the driver's body part, the controller 130 may apply a control signal to the transducer elements 121a of the fourth group G4 corresponding to the left cheek of the driver.

In addition, when the controller 130 determines that the driver's head is facing downward, the controller 130 may control the haptic stimulator 120 to transmit an ultrasonic beam to the driver's cheek.

In addition, when the controller 130 determines that the driver's head is facing forward, but the gaze is not facing forward, the haptic stimulator 120 can be controlled to send an ultrasonic beam to the driver's eyes.

When the controller 130 controls the haptic stimulator 120 to generate an ultrasonic beam, the distance between the haptic stimulator 120 and the target position, that is, the driver, may also be considered. In this case, the information about the distance between the haptic stimulator 120 and the driver may be obtained from an image acquired by the stereo camera, or may be obtained based on the information about the position of the driver's seat 72.

The controller 130 may determine the driver's state in real time or periodically, and after the haptic stimulus is started, if the driver's state no longer corresponds to a warning target state such as waking from drowsiness or looking forward, the haptic stimulus may be stopped. That is, the transmission of the ultrasonic beam can be stopped.

The controller 130 may increase the intensity of the ultrasonic beam when the driver's state still corresponds to the warning target state even after the reference time has elapsed since the provision of the haptic stimulus. For example, the intensity of the ultrasonic beam may be divided into 1, 2, and 3 stages, and the intensity of the ultrasonic beam may be set to increase from 1 to 3 stages. The initial provision of the haptic stimulus can set the intensity of the ultrasonic beam in first step, and if the driver's condition is first re-determined after the provision of the haptic stimulus is started, the intensity of the ultrasonic beam is increased in second steps if it still corresponds to the warning target state. If it is determined again afterwards, the intensity of the ultrasonic beam can be increased in third stages if it still corresponds to the warning target state.

In addition, when the driver's state corresponds to a drowsy state, the controller 130 may control the haptic stimulator 120 to transmit a stronger ultrasonic beam than when the driver's state corresponds to a drowsy state.

Hereinafter, a driver state warning method according to one form will be described. In the driver state warning method, the above-described driver state warning apparatus 100 and the vehicle 1 including the same may be applied. Therefore, the contents described above with reference to FIGS. 1 to 15 may be applied to the form of the driver status warning method even if not mentioned otherwise.

Figure 16:
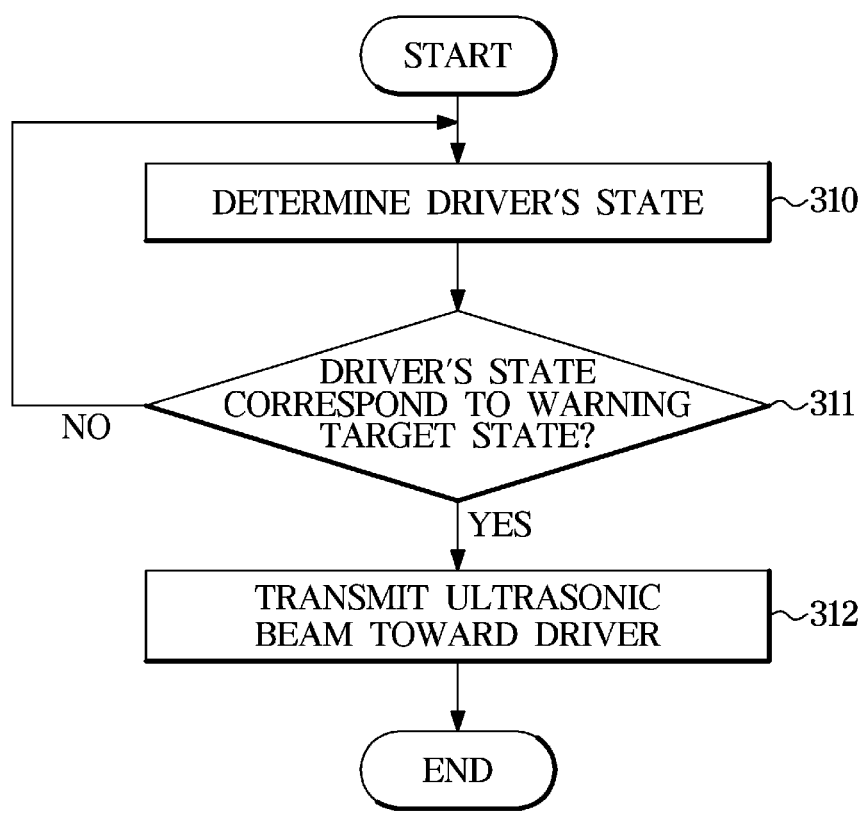
FIG. 16 is a flowchart illustrating a driver state warning method.

FIG. 16 is a flowchart illustrating a driver state warning method according to one form.

According to the driver condition warning method shown in FIG. 16, the controller 130 may determine the driver's state based on an output value of the detector 110 that acquires information related to the driver's state (310). For example, the detector 110 may include a camera 111 for capturing an image of a driver and may include a bio signal sensor. The description of detector 110 is as described above.

When the camera 111 determines the driver's state based on the captured image of the driver, the controller 130 may determine whether the driver's state corresponds to a drowsy state or a careless state. Drowsiness and careless state are included in a state in which a warning should be output by providing a haptic stimulus to the driver, that is, in a state of being alerted.

When the driver's state corresponds to the warning target state (YES in 311), the ultrasonic beam is sent toward the driver (312). Sending the ultrasonic beam toward the driver may include the controller 130 determining a target position to send the ultrasonic beam in the driver's image. For example, if the driver's state corresponds to the drowsiness state, the target position may be the position of the driver's eyes, and if the driver's state corresponds to the careless state, the target position may be determined according to the direction in which the head of the driver faces.

On the other hand, the type of haptic stimulation can be changed by adjusting the speed of the ultrasonic signal, so that a short wave ultrasonic signal can be provided to provide a vibration stimulus to the driver and a long wave ultrasonic signal can be provided to the driver to provide a resistive stimulus.

In addition, transmitting the ultrasonic beam toward the driver may further include controlling the transducer array 121 to transmit the ultrasonic beam to the target position by the controller 130. In detail, the controller 130 may determine the position of the transducer element 121a corresponding to the target position, and provide a haptic stimulus to the body part of the target position by transmitting a control signal to the transducer element 121a at the determined position.

As described above, the plurality of transducer elements 121a are divided into a plurality of groups according to the driver's body parts (eyes, left cheeks, right cheeks, chin, etc.), the controller 130 may transmit the control signal to the transducer element 121a of the group corresponding to the body part included in the target position to generate the ultrasonic beam.

Alternatively, the position information of the driver's image and the position information of the transducer array 121 may be matched and stored, and the control signal may be transmitted to the transducer elements 121a matched to the target position.

Alternatively, the directional ultrasonic beam focused on the target position may be generated by controlling the phase of the ultrasonic signal generated by each transducer element 121a without changing the position of the transducer element 121a used for each target position.

Figure 17:
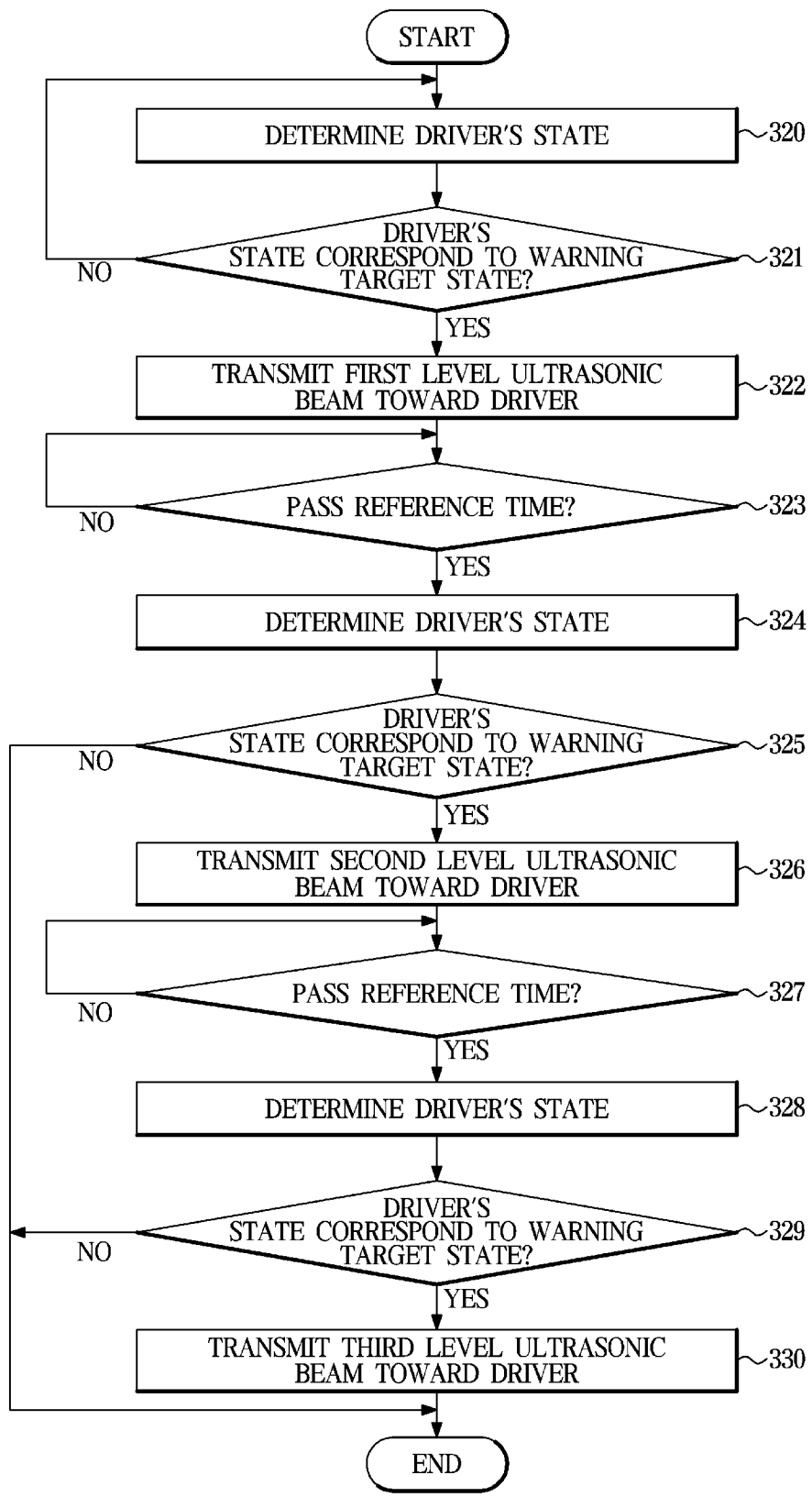
FIG. 17 is another flowchart illustrating a driver state warning method.

FIG. 17 is another flowchart illustrating a driver state warning method according to another form.

Referring to FIG. 17, the driver state warning method includes: determining a driver's state (320), and if the driver's state corresponds to a warning target state (YES of 321), sending an ultrasonic beam toward the driver (322). Up to this point, the same information as described above with reference to steps 310 to 312 described with reference to FIG. 16 is described.

However, the intensity of the ultrasonic beam transmitted toward the driver may vary from step to step. If the driver's condition still corresponds to the warning target state even after a predetermined time has elapsed since the provision of the haptic stimulus, the intensity of the ultrasonic beam may be increased. For example, the intensity of the ultrasonic beam may be divided into 1, 2, and 3 stages, and the intensity of the ultrasonic beam may be set to increase from 1 to 3 stages.

When the ultrasonic beam is first transmitted, the ultrasonic beam of first stage is transmitted (322), and when the reference time passes (Yes of 323), the driver's state is determined again (324).

If the driver's condition still corresponds to the warning target state (Yes of 325), the ultrasonic beam of the second stage is sent to the driver (326). If the reference time passes again (Yes of 327), the state of the driver is determined again (328), and if the state of the driver still corresponds to the warning target state (Yes of 329), the ultrasonic beam of the third stage is transmitted toward the driver (330). The reference time in step 327 may be the same as the reference time in step 323, may be shorter, or longer.

At any stage, if the driver's condition no longer corresponds to the warning target condition (NO in 325, NO in 329), the transmission of the ultrasonic beam may be stopped.

Alternatively, the intensity of the ultrasonic beam may be controlled differently when the driver's state corresponds to the drowsy state and when the driver's state corresponds to the careless state. For example, when the driver's state corresponds to a drowsy state, the haptic stimulator 120 may be controlled to transmit a stronger ultrasonic beam than when the driver's state corresponds to a careless state.

According to the driver state warning device, a vehicle including the same, and a driver state warning method according to the above-described form, by providing haptic stimuli in a non-contact manner to drivers in drowsy or careless states, safe driving can be induced by effective and direct attention.

As described above, the disclosed forms have been described with reference to the accompanying drawings. Although example forms of the disclosure have been shown and described, it would be appreciated by those skilled in the art that changes may be made to these forms without departing from the principles and spirit of the disclosure.

In accordance with an aspect, a driver state warning apparatus, a vehicle, and a driver state warning method are capable of providing a safe and effective driving directly by non-contact haptic stimulus to a driver using an ultrasonic signal when the driver is in a drowsy or careless state.

DESCRIPTION OF SYMBOLS

100: Driver state warning apparatus
110: detector
120: haptic stimulator
130: controller
1: vehicle

What is claimed is:

1. A driver state warning apparatus comprising:
a detector configured to obtain state information of a driver;
a haptic stimulator configured to generate an ultrasonic beam and transmit the generated ultrasonic beam; and
a controller configured to:
determine whether a state of the driver corresponds to a predetermined warning target state based on the obtained state information of the driver,
provide a non-contact haptic stimulus by transmitting the ultrasonic beam toward the driver by controlling the haptic stimulator when the state of the driver corresponds to the warning target state, and
transmit the ultrasonic beam towards an eye of the driver by controlling the haptic stimulator when the state of the driver corresponds to a drowsy state.

2. The driver state warning apparatus according to claim 1, wherein
the haptic stimulator includes a transducer array configured to convert an electrical signal into an ultrasonic signal.

3. The driver state warning apparatus according to claim 2, wherein
the detector includes a camera configured to capture an image of the driver.

4. The driver state warning apparatus according to claim 3, wherein
the controller is configured to:
determine a target position to transmit the ultrasonic beam from the image of the driver, and
control the transducer array to transmit the ultrasonic beam to the target position.

5. The driver state warning apparatus according to claim 4, wherein:
the transducer array includes a plurality of transducer elements which are divided into a plurality of groups based on body parts of the driver, and
the controller is configured to transmit a control signal to transducer elements of a group, among the plurality of groups, corresponding to a body part of the driver included in the target position.

6. The driver state warning apparatus according to claim 4, wherein
the controller is configured to:
match and store location information of the image of the driver and location information of the transducer array, and
transmit a control signal to the transducer array matched to the target position.

7. The driver state warning apparatus according to claim 4, wherein
the controller is configured to control the transducer array to generate a directional ultrasonic beam directed towards the target position.

8. The driver state warning apparatus according to claim 3, wherein:
the controller is configured to:
determine whether the state of the driver corresponds to at least one of the drowsy state or a careless state based on the image of the driver, and
transmit the ultrasonic beam towards at least one body part of the driver by controlling the haptic stimulator when the state of the driver corresponds to the at least one of the drowsy state or the careless state.

9. The driver state warning apparatus according to claim 8, wherein
the controller is configured to stop transmitting the ultrasonic beam after start of transmitting the ultrasonic beam when the state of the driver does not correspond to at least one of the drowsy state or the careless state.

10. The driver state warning apparatus according to claim 1, wherein
the controller is configured to transmit a short wave ultrasonic beam by controlling the haptic stimulator to provide a vibration stimulus to the eye.

11. The driver state warning apparatus according to claim 1, wherein
the controller is configured to determine whether the state of the driver corresponds to a careless state based on an image of the driver.

12. The driver state warning apparatus according to claim 11, wherein
the controller is configured to transmit the ultrasonic beam from a direction of a face of the driver by controlling the haptic stimulator when the state of the driver corresponds to the careless state.

13. The driver state warning apparatus according to claim 12, wherein
the controller is configured to transmit a long wave ultrasonic beam by controlling the haptic stimulator to provide a resistive stimulus in a direction opposite to a direction currently facing the face of the driver.

14. The driver state warning apparatus according to claim 11, wherein
the controller is configured to transmit the ultrasonic beam toward the eye by controlling the haptic stimulator when the state of the driver corresponds to the careless state.

15. A vehicle, comprising:
a detector configured to obtain information regarding a state of a driver;
a haptic stimulator configured to generate an ultrasonic beam and transmit the generated ultrasonic beam; and
a controller configured to:
determine whether the state of the driver corresponds to a predetermined warning target state based on the obtained information regarding the state of the driver,
provide a non-contact haptic stimulus by transmitting the ultrasonic beam toward the driver by controlling the haptic stimulator when the state of the driver corresponds to the warning target state, and transmit the ultrasonic beam towards an eye of the driver by controlling the haptic stimulator when the state of the driver corresponds to a drowsy state.

16. The vehicle according to claim 15, wherein
the haptic stimulator includes a transducer array configured to convert an electrical signal into an ultrasonic signal.

17. A driver state warning method, the method comprising:
   obtaining, by a detector, information regarding a state of a driver;
   determining, by a controller, whether the state of the driver corresponds to a predetermined warning target state; and
   providing, by the controller, a non-contact haptic stimulus by transmitting an ultrasonic beam toward an eye of the driver by controlling a haptic stimulator including a plurality of transducer arrays when the state of the driver corresponds to the warning target state including a drowsy state.

18. The method according to claim 17, wherein
obtaining information regarding the driver state includes capturing an image of the driver by using a camera.

19. The method according to claim 18, wherein transmitting the ultrasonic beam toward the eye of the driver includes:
   determining a target position to transmit the ultrasonic beam from the image of the driver, and
   controlling the plurality of the transducer arrays to transmit the ultrasonic beam to the target position.

* * * * *